United States Patent [19]

Clausen et al.

[11] Patent Number: 4,975,093
[45] Date of Patent: Dec. 4, 1990

[54] HAIR DYEING COMPOSITIONS CONTAINING 2,6-DINITRO-PHENOL-DERIVATIVES

[75] Inventors: Thomas Clausen; Wolfgang Balzer, both of Alsbach; Günther Lang, Reinheim, all of Fed. Rep. of Germany

[73] Assignee: Wella Aktiengesellschaft, Darmstadt, Fed. Rep. of Germany

[21] Appl. No.: 385,560

[22] Filed: Jul. 24, 1989

[30] Foreign Application Priority Data

Jul. 23, 1988 [DE] Fed. Rep. of Germany ....... 3825163

[51] Int. Cl.$^5$ ..................... A61K 7/13; C09B 67/00; C07C 205/00
[52] U.S. Cl. .......................... 8/428; 8/429; 8/414; 8/401; 8/405; 8/421; 568/706
[58] Field of Search ................. 8/428, 429, 401, 405, 8/409; 568/706

[56] References Cited

U.S. PATENT DOCUMENTS

| | | | |
|---|---|---|---|
| 4,125,601 | 11/1978 | Bugaut et al. | 424/71 |
| 4,152,112 | 5/1979 | Bugaut | 8/410 |
| 4,311,478 | 1/1982 | Bugaut | 8/407 |
| 4,390,341 | 6/1983 | Jacobs | 8/424 |
| 4,432,769 | 2/1984 | Bugaut | 8/414 |
| 4,543,425 | 9/1985 | Konrad | 564/442 |
| 4,575,378 | 3/1986 | Seidel et al. | 8/414 |
| 4,637,821 | 1/1987 | Monnais et al. | 8/428 |
| 4,664,845 | 5/1987 | Jancis et al. | 252/401 |
| 4,704,474 | 11/1987 | Konrad | 564/441 |
| 4,725,282 | 2/1988 | Hoch et al. | 8/405 |
| 4,764,174 | 8/1988 | Hoshowski | 8/415 |
| 4,797,130 | 1/1989 | Clausen et al. | 8/409 |
| 4,835,314 | 5/1989 | Konrad et al. | . |
| 4,838,894 | 6/1989 | Kijek et al. | 8/412 |

FOREIGN PATENT DOCUMENTS

2327987 6/1973 Fed. Rep. of Germany .......... 8/429

OTHER PUBLICATIONS

Hawley's Condensed Chemical Dictionary, N. Irving Sax et al., 11th Edition, Van Nostrand Reinhold Co., N.Y. pp. 421.

*Primary Examiner*—Paul Lieberman
*Assistant Examiner*—James M. Silbermann
*Attorney, Agent, or Firm*—Michael J. Striker

[57] ABSTRACT

The hair dyeing composition in the form of an aqueous solution, an aqueous-alcoholic solution, a cream, a gel, a mixture which can be sprayed or an emulsion contains from 0.01 to 2.0% of a 2,6-Dinitro-phenol derivative of the formula (I):

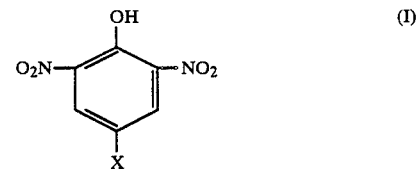

wherein X represents a member selected from the group consisting of alkyl groups containing one to four carbon atoms, monohydroxyalkyl groups containing one to four carbon atoms, perfluoroalkyl groups containing one to four carbon atoms, alkoxy groups containing one to four carbon atoms, monohydroxyalkoxy groups containing two to four carbon atoms, dihydroxyalkoxy groups containing three to four carbon atoms and halogens, and one or more cosmetic additives selected from the group consisting of glycerin, glycols, glycol ethers, hair car materials, wetting agents and emulsifiers, thickeners, softeners, preservatives, complexing agents and perfumes. The dyes of the formula (I) have good physiological properties and provide a variety of yellow shades. The hair dyeing compositions also advantageously comprise a 2,6-Dinitro-phenol derivatives of formula I and a known oxidizing hair dye or direct hair dye as well as one or more of the above cosmetic additives. The dyes having the general formla (I) have good physiological properties and provide all the yellow shades required to dyeing form a bluish lemon-yellow to a pure yellow to a red-orange.

10 Claims, No Drawings

HAIR DYEING COMPOSITIONS CONTAINING 2,6-DINITRO-PHENOL-DERIVATIVES

BACKGROUND OF THE INVENTION

Our invention relates to a nitrodye used for dyeing hair and to a method of dyeing hair using a nitrophenol derivative as the nitrodye.

Nitrodyes currently are widely used in hair coloring agents. They are used in oxidizing hair dyeing compositions as additives for producing natural color shades or artificial color tones which are currently in fashion. By combinations of several different colored nitrodyes it is possible to produce a hair dyeing composition which can dye the hair in natural to artificial shades without use of oxidizing agents.

Thus natural brown colors can be used for example by combination of an orange with a blue nitrodye. Besides it is also possible to combine yellow colored with violet colored nitrodyes to obtain a similar result. Yellow nitrodyes are necessary, which are able to dye the hair either in an intense pure lemon yellow, which must be as free as possible of red component or orange colors and which can be used in combination with blue colors.

There are many other additional requirements however for a hair dyeing composition. The nitrodye must be unquestionable in regard to toxicological and dermatological considerations.

Their use in oxidizing hair dyeing compositions presupposes that they are stable in the presence of hydrogen peroxide in an alkaline solution. Moreover a good light-fastness, acid-fastness and fastness to rubbing is required. Finally the nitrocompounds should be made by the simplest possible process.

The nitrophenol and aminonitrophenols currently described in the literature do not or insufficiently fulfill the previously described prerequisites. Scarcely any hair coloring results from using 2-nitro-phenols. The 4-Nitro-3-(2'-hydroxyethyl)amino-phenol cited in International Journal of Cosmetic Scienc pp. 25 to 35 of course produces a lemon-yellow color but it is however a very weak color. Two additional isomers, namely the nitro and the 5-nitro-2-(2'-hydroxyethyl)amino-phenol, are pH sensitive and show undesirable color changes under action by acid or alkali.

Additional known yellow nitrodyes are the o-, m-, and p-Nitroaniline derivatives taught in German Patent Document 1 619 395. These compounds largely fulfill the requirements regarding dye technology considerations but are not satisfactory in regard to the physiological properties.

The 2-Nitro-aniline derivatives described in German Open Patent Application 3 442 757 largely fulfill the requirements, however the shades of color attainable by variation of the substituents do not extend to the red regions. Thus no fashionable artificial red hair colors can be produced without the additional use of red dyes with the previously described 2-Nitro-aniline derivatives.

Besides it is difficult to obtain a uniform coloring of the hair over the length of the hairs using a hair dyeing compositions having a mixture of dyes, since they are damaged usually at the ends and thus have a more porous surface there than at the hair roots.

A uniform dyeing can be attained, when dyes of the same basic structure are used, which correspond in their selectivity and in their developing ability.

Using dyes of the same structure has the advantage that these dyes also have the same properties in regard to light fastness and washability. Thus for example color differences caused by washing out a dye from a dye mixture by repeated shampooing are avoided.

SUMMARY OF THE INVENTION

Accordingly, it is an object of our invention to provide nitrodyes for use in a hair dye which have the advantageous properties of compounds according to German Patent Open Patent Application 3 442 757 but also allow extension of the color shades into the red region(by variation of substituents).

In keeping with these objects and with others which will become apparent hereinafter, a hair dye useful in a hair dyeing composition comprises a 2,6-dinitro-phenol-derivative of the formula(I)

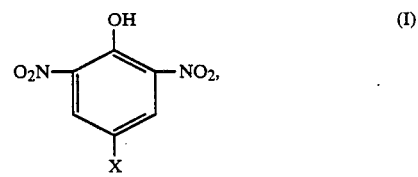

in which X represents an alkyl group containing one to four carbon atoms, a monohydroxyalkyl group containing one to four carbon atoms, a perfluoroalkyl group containing one to four carbon atoms, alkoxy group containing one to four carbon atoms, a monohydroxyalkoxy group containing two to four carbon atoms, dihydroxyalkoxy group containing three to four carbon atoms or halogens.

These compounds satisfy the objects of the invention in an outstanding way.

By variation of the structure of the X group in the compounds of the formula(I) all the required color tones are provided from the bluish lemon-yellow to pure yellow and to an orange-red.

In comparison to the dyes of the 2-Nitro aniline type according to the German Open Patent Application 3 442 757 with the compounds of the general formula (I) the available color tones are extended into the red region. Hereby it is possible to produce not only natural brown colors with suitable blue or violet dyes, but also fashionable red hair colors with other basic structures without the additional application of red dyes.

Also in keeping with the above-mentioned objects of the invention a dye useful in a hair dyeing composition but which is omitted from the above-mentioned dyes because of physiological and dye characteristics comprises a 2,6-Dinitro-phenol-derivative of the general formula(II):

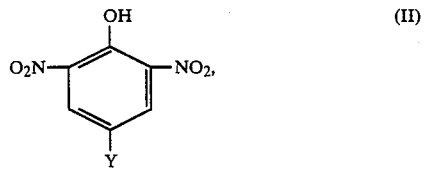

in which Y represents the $CH_3$ group, $C(CH_3)_3$ group, $CF_3$ group, $CH_2OH$ group, $OCH_3$ group, Cl or Br.

For example 2,6-Dinitro-4-methyl-phenol, 2,6-Dinitro-4-trifluoromethyl-phenol, 2,6-Dinitro-4-methoxy-phenol, 4-Chloro-2,6-dinitro- phenol and 4-Bromo-2,6- dinitro-phenol are suitable 2,6-Dinitro-phenol derivatives of the general formula (I).

The compounds of the general formula (I) provide extraordinarily suitable Nitro color dyes in the yellow to red range which are suitable for coloring human hair. They are soluble in water and have a distinguished storage stability.

Compounds of the general formula (I) have surprisingly good physiological properties. Thus Dinitrophenols with $X=C(CH_3)_3$, $CF_3$ and Br show no mutagenic effect in an Ames test.

One object of the present invention is thus to provide an agent for coloring hair with a dye content and cosmetic additives which are standard in these hair dyeing compositions in which a 2,6-Dinitrophenol derivative of the general formula(I), advantageously in a quantity of from 0.01 to 2.0 weight percent, is contained.

The hair dyeing composition according to our invention can be provided in one embodiment in which it is applied without application of an oxidizing agent and also another embodiment in which the addition of an oxidizing agent is required.

In the first embodiment without added oxidizing agent the hair dyeing composition contains other known dyes going on the hair directly besides the dye of the given general formula(I). Of these known dyes for hair dyeing the following should be mentioned, such as e.g. 2-Amino-4-nitro-phenol, Picramic acid, 2-(2'-Hydroxyethyl)amino-4,6-dinitro-benzene, 1-(2'-Hydroxyethyl)amino-4-nitro-benzene, 4-(2'-Ureidoethyl)amino- nitrobenzene, 4-(2',3'-Dihydroxypropyl) amino-3-nitro- trifluoromethyl benzene, 1,4-Bis(2'-hydroxyethyl)amino-4-N-ethyl-2-nitro-benzene, 4-(2'-Hydroxyethyl)amino-3-nitro-toluene, 2-Nitro-4-(2'-hydroxyethyl) amino-aniline, 2,5-Bis(2'-hydroxyethyl) amino-nitrobenzene, 2-(2'-hydroxyethyl)amino- 4,6-dinitro-phenol, 1-Amino-4-(2',3'-dihydroxypropyl) amino-2-nitro-5-chloro-benzene, 4-Bis(2'-hydroxyethyl) amino-1-(2'-hydroxyethyl)-amino-2-nitro-benzene, 1-Amino-2-nitro-4-bis(2'-hydroxyethyl)amino-benzene; Triphenyl methane dyes, such as Basic Violet 1 (C.I. 42535); Azodyes, such as Acid Brown 4 (C.I. 14805); Anthraquinone dyes, such as Disperse Blue 23 ( C.I. 61545), Disperse Violet 4 (C.I. 61105), 1,4,5,8-Tetraamino-anthraquinone and 1,4-Diamino-anthraquinone, dyes of this class having an acidic, nonionigenic or basic character according to their substituents. Other suitable dyes put directly on the hair are for example described in a Book by J. C. Johnson, "Hair Dyes", Noyes Data Corp., Park-Ridge(USA) (1973), pp. 3 to 91 and 113 to 139(ISBN:0-81555-0477-2).

The form of the hair dyeing composition preparation described here on the basis of dyes directly applied to the hair can advantageously be a solution, especially an aqueous or an aqueous-alcoholic solution. It can also be in the form of a cream, a gel or an emulsion. It can be sprayed in a mixture with a propellant gas or by a pump.

The dye of the general formula (I) should be contained in this hair dyeing composition without an oxidizing agent-additive in a concentration of about 0.01 to 2.0 percent by weight, advantageously from 0.01 to 1.0 percent by weight. The total content of dye applied directly to hair is approximately in a range of from about 0.01 to 3.0 percent by weight.

The pH-value of this dye is in a range from 3 to 10.5, especially from 7.5 to 9.5. The adjustment of the desired alkaline pH-value advantageously occurs with ammonia, however an organic amine, e.g. monoethanol amine or triethanol amine, can also be used.

Its application occurs in a standard way by application of a hair dyeing composition to the hair. This hair dyeing composition remains in contact with the hair for a comparatively long time, for about 5 to 30 minutes. Subsequently the hair is rinsed with water, if necessary with an aqueous solution of a weak organic acid, and thus is dried. Acetic acid, citric acid, tartaric acid and others can be used.

The hair dyeing composition without oxidizing agent additive previously described can also include a cosmetic polymerizate so that the hair can be simultaneously set or fixed. Such agents are generally called dyeing and setting or tinting and setting agents.

Of the known polymers used in cosmetics polyvinyl pyrrolidone, polyvinyl acetate, polyvinyl alcohol or polyacrylic compounds like polyacrylic acid and polymethacrylic acid polymerizate, basic polymerizates of esters made from these compounds and aminoalcohols or their salts and quaternary products, polyacrylic nitrile, polyvinyl lactam and copolymerizates made from compounds of this type, e.g. polyvinyl pyrrolidone-vinyl acetate.

Also natural polymers such as Chitosan(deacatylated Chitin) or Chitosan derivatives can be used for the above-named purpose.

The polymerizates are contained in these hair coloring agents in quantities for about 1 to 5 percent by weight. The pH-values of these hair dyeing compositions are in the vicinity of about 6.0 to 9.0.

The use of these hair dyeing compositions with additional hair setting occurs in a known and conventional way by moistening the hair with a setting agent, which sets the hair, and subsequent drying.

Understandably the above described hair dyeing agent without oxidizing agent additive can if necessary contain conventional additives for hair dyeing compositions such as hair care materials, wetting agents, thickeners, softeners, preservatives and perfume oils as well as other conventional additives for oxidizing dye agents.

As mentioned previously the objects of the present invention are also satisfied in a hair dyeing composition in which there is an additive oxidizing agent. It contains in addition to the dyes according to the given general formula (I) and if necessary known dyes applied directly to the hair additional known oxidation dyes, which need an oxidative development.

In this oxidizing dye it is chiefly a matter of an aromatic p-Diamine and p-Amino phenol, such as p-Toluene diamine, p-Phenylene diamine, p-Aminophenol and similar compounds, which are combined with so-called modifiers, such as e.g. m-Phenylene diamine, Resorcinol, m-Aminophenol and other compounds for the purpose of producing nuances of color.

This kind of conventional oxidizing dye known for hair coloring is among other things described in the book of E.Sagarin, "Cosmetics" Science and Technology(1957), Interscience Publishers Inc., New York, p. 503 ff. and in the book by H.Janistyn, "Handbook of Cosmetics and Perfumes" (1973), p. 228 ff.

With mixtures of these oxidizing dyes and the dyes according to the general formula (I) very good natural blond and brown shades may be produced, however also result fashionable artificial colors as well.

The dyes according to formula (I) are contained in this coloring agent with oxidizing agent-additive in a concentration of about 0.01 to 2.0 percent by weight, advantageously 0.01 to 1.0 percent by weight. The total content of dye in this coloring agent amounts to about 0.1 to 5.0 percent by weight.

Oxidizing hair dyeing compositions are generally alkaline, advantageously with a pH-value of about 8.0 to 11.5. This pH is attained chiefly by adjustment with ammonia. Another organic amine, e.g. monoethanol amine or triethanol amine, can be used. As an oxidizing agent for development of hair color primarily hydrogen peroxide and its addition compounds are used. The form of the hair dyeing preparations can be the same as with the hair dyeing composition without the oxidizing agent-additive. Advantageously they are in the form of a cream or a gel.

Additional additives in creams, emulsions or gels include solvents such as water, lower aliphatic alcohols, e.g. ethanol, propanol, isopropanol, glycerin or glycols, e.g. ethylene glycols and propylene glycols, or also glycol ethers, wetting agents or emulsifiers from the class of anionic, cationic, amphoteric or nonionogenic surface active substances, such as fatty alcohol sulfates, fatty alcohol ether sulfates, alkyl sulfonates, alkyl benzene sulfates, alkyl trimethyl ammonium salts, alkyl betain, ethoxylated fatty alcohols, ethoxylated fatty acid esters, thickeners, such as higher fatty alcohols, bentonite, starch, polyacrylic acid, cellulose derivatives such as carboxymethyl cellulose, alginate, vaseline, paraffin oil and fatty acids as well as hair care materials such as lanolin derivatives, cholesterol, pantothenic acid and betain as well as perfumes and complexing agents. The mentioned components are used in their standard amounts, e.g. the wetting agent and the emulsifiers are used in a concentration of about 0.5 to 30 percent by weight, while the thickener can be contained in an amount of from about 0.1 to 5 percent by weight in the preparation.

The use of the above-mentioned preparations, in which the addition of an oxidizing agent is required, occurs in a known way, when one mixes the hair dyeing composition before treatment with the oxidizing agent and applies a quantity of the mixture sufficient to color the hair, generally about 50 to 150 ml, to the hair. After an acting time sufficient for hair coloring, which is about 10 to 45 minutes, the hair is rinsed with water, if necessary subsequently with an aqueous solution of a weak organic acid, such as citric acid or tartaric acid, and then dried.

A wide range of different tones and shades of color are available using the hair dyeing composition according to our invention. These include natural shades to very fashionable artificial bright colors. The coloring agent of each composition are either applied in combination with hydrogen peroxide or also without an oxidizing agent.

The 2,6-Dinitro-phenol derivatives of the formula (I) are known in part. For example the making of the following compounds is described in the Literature in the following Table :

TABLE

| Compound | PRODUCTION PROCESS LITERATURE. Reference |
|---|---|
| $CH_3$ | G. G. S. Dutton, T. I. Briggs, B. R. Brown and M. E. D. Hillman: Can. J. Chem. 31, 685 (1953). |
| $C_2H_5$ | G. G. S. Dutton, T. I. Briggs, B. R. Brown and M. E. D. Hillman: Can. J. Chem. 31, 837 (1953). |
| $C_3H_7$ | G. G. S. Dutton, T. I. Briggs, B. R. Brown and M. E. D. Hillman: Can. J. Chem. 31, 685, 837 (1953). |
| $C_4H_9$ | G. G. S. Dutton, T. I. Briggs, B. R. Brown and M. E. D. Hillman: Can. J. Chem. 31, 837, 1138 (1953). |
| $CF_3$ | Jagupolskii and Mospan: Ukr. Chim. Z. 21, 81 (1955); C.A. 1955, 8866. |
| Cl | U. Kohn and R. Kramer, Monatsh. 49, 154 (1923). |
| Br | E. Sakellarios: Chem. Ber. 55,2846 (1922). |
| $OCH_3$ | W. B. Shaw: J. Chem. Soc. 99, 1613 (1911). |
| $CH_2OH$ | US-PS 4,661,382. |

The rest of the compounds of the general formula (I) may be synthesized by processes analogous to those described in the above Table.

The following examples should further more clearly illustrate our invention without limiting the appended claims which define it.

EXAMPLES

EXAMPLE I

Hair Dyeing liquid

| | |
|---|---|
| 0.30 g | 2,6-Dinitro-4-methoxy-phenol |
| 2.00 g | Lauryl alcohol-diglycol ether sulfate sodium salt (28% aqueous solution) |
| 2.00 g | Ammonia (25% aqueous solution) |
| 95.70 g | Water |
| 100.00 g | |

Bleached natural hair is treated 20 minutes long at room temperature with a solution according to example 1, after which the hair is rinsed with water and subsequently dried. The hair is dyed a bright red-orange.

EXAMPLE II

Dyeing and Setting Solution

| | |
|---|---|
| 0.10 g | 2,6-Dinitro-4-trifluoromethyl-phenol |
| 2.00 g | Polyvinyl pyrrolidone |
| 0.10 g | Glycerin |
| 40.00 g | Isopropanol |
| 57.80 g | Water |
| 100.00 g | |

White human hairs are moistened with dyeing and setting solution, curled with curlers and dried. Subsequently the curlers are removed and the hair combed into a hairdo. The hair is colored bright lemon-yellow and set.

EXAMPLE III

Oxidizing Hair Dyeing Composition in Cream Form

| | |
|---|---|
| 0.10 g | 4-Bromo-2,6-dinitro-phenol |
| 0.20 g | p-Phenylenediamine |
| 0.15 g | Resorcinol |
| 0.03 g | m-Aminophenol |
| 15.00 g | Cetyl alcohol |
| 3.50 g | Lauryl alcohol-diglycol ether sulfate-sodium salt (28% aqueous solution) |
| 6.00 g | ammonia (25% aqueous solution) |
| 75.02 g | water |
| 100.00 g | |

50 g of the above hair dyeing composition are mixed shortly before application with 50 ml of 6% aqueous hydrogen peroxide solution. The mixture is subsequently applied to gray human hair and allowed to act for 30 minutes at a Temperature of 40° C. After rinsing hair with water and subsequent drying it takes a fashionable blond shade.

EXAMPLE IV

Hair Dyeing Cream

| | |
|---|---|
| 0.05 g | 4-Chloro-2,6-Dinitro-phenol |
| 0.25 g | 4-Ethyl-(2'-hydroxyethyl)amino-1-(2'-hydroxyethyl)amino-2-nitro-benzene |
| 0.02 g | 1-Amino-2-nitro-4-bis(2'-hydroxyethyl)amino-benzene |
| 0.025 g | Disperse Blue 23 (C.I. 61545) |
| 7.500 g | Cetyl alcohol |
| 1.750 g | Lauryl alcohol-diglycol ether sulfate-Sodium salt (28% aqueous solution) |
| 0.100 g | p-Hydroxybenzoic acid methyl ester |
| 0.200 g | Ammonia (25% aqueous solution) |
| 90.105 g | water |
| 100.00 g | |

50 g of this hair coloring cream is applied to white human hair and after acting for 20 minutes is rinsed with water. The hair is subsequently dried. It is colored in a natural brown shade.

EXAMPLE V

Hair Dyeing Liquid

| | |
|---|---|
| 0.25 g | 2,6-Dinitro-4-methoxy-phenol |
| 0.10 g | 1-amino-4-(2',3'-dihydroxypropyl)amino-2-nitro-5-chloro-benzene |
| 0.20 g | 4-Ethyl-(2'-hydroxyethyl)amino-1-(2'-hydroxyethyl)amino-2-nitro-benzene |
| 0.50 g | Hydroxyethylcellulose |
| 5.00 g | Lauryl alcohol-diglycol ether sulfate-Sodium salt (28% aqueous solution) |
| 10.00 g | Isopropanol |
| 10.00 g | Ammonia (25% aqueous solution) |
| 73.95 g | Water |
| 100.00 g | |

Bleached natural hair is treated for 20 minutes at room temperature with the solution according to this example. After rinsing the hair with water and subsequent drying the hair is dyed in a fashionable Beaujolais color.

EXAMPLE VI

Hair Dyeing Liquid

| | |
|---|---|
| 0.30 g | 4-Bromo-2,6-dinitro-phenol |
| 0.05 g | 1,4-Bis(2'-hydroxyethyl)amino-2-nitro-benzene |
| 0.50 g | Hydroxyethylcellulose |
| 5.00 g | Lauryl alcohol-diglycol ether sulfate-Sodium salt (28% aqueous solution) |
| 10.00 g | Isopropanol |
| 10.00 g | Ammonia (25% aqueous solution) |
| 74.15 g | Water |
| 100.00 g | |

This coloring agent is allowed to act on bleached hair for about 30 minutes at 30° C. After rinsing the hair with water and subsequent drying the hair is colored in a fashionable bright blond shade.

It will be understood that each of the elements described above, or two or more together, may also find a useful application in other types of constructions differing from the types described above.

While the invention has been illustrated and described as embodied in a hair dye for a hair dyeing composition containing 2,6-dinitro-phenol-derivatives and a method of dyeing hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims.

1. A hair dyeing composition in the form of an aqueous solution, an aqueous-alcoholic solution, a cream, a gel, a mixture which can be sprayed or an emulsion comprising an effective amount of a 2,6-Dinitro-phenol derivative of the general formula (I),

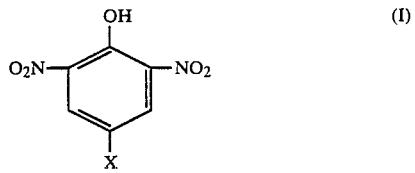

wherein X represents a member selected from the group consisting of alkyl groups containing one to four carbon atoms, monohydroxyalkyl groups containing one to four carbon atoms, perfluoroalkyl groups containing one to four carbon atoms, alkoxy groups containing one to four carbon atoms, monohydroxyalkoxy groups containing two to four carbon atoms, dihydroxyalkoxy groups containing three to four carbon atoms and halogens, and, in addition to a member selected from the group consisting of water, aliphatic alcohols, and mixtures of water and said alcohols; one or more additives selected from the group consisting of glycerin, glycols, glycol ethers, hair care materials, wetting agents and emulsifiers; anionic cationic, amphoteric and nonionogenic surface active substances, thickeners, softeners, preservatives, complexing agents and perfumes.

2. A hair dyeing composition in the form of an aqueous solution, an aqueous-alcoholic solution, a cream, a gel, a mixture which can be sprayed or an emulsion comprising an effective amount of a 2,6-Dinitro-phenol derivative of the general formula (II),

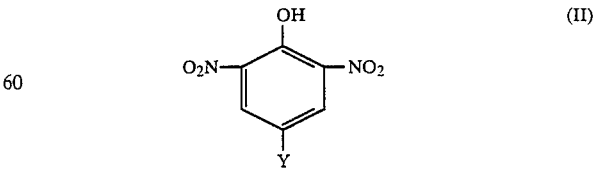

wherein Y represents a member selected from the group consisting of $CH_3$, $C(CH_3)_3$, $CF_3$, $CH_2OH$, $OCH_3$, $Cl$ and $Br$, and, in addition to a member selected from the group consisting of water, aliphatic alcohols, and mixtures of water and said alcohols; one or more additives selected from the group consisting of glycerin, glycols, glycol ethers, hair care materials, wetting agents and emulsifiers; anionic, cationic, amphoteric and nonionogenic surface active substances, thickeners, softeners, preservatives, complexing agents and perfumes.

3. A hair dyeing composition in the form of an aqueous solution, an aqueous-alcoholic solution, a cream, a gel, a mixture which can be sprayed or an emulsion containing from 0.01 to 2.0% of a 2,6-Dinitro-phenol derivative of the general formula (I):

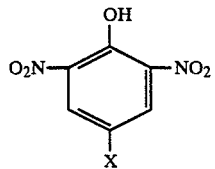

wherein X represents a member selected from the group consisting of alkyl groups containing one to four carbon atoms, monohydroxyalkyl groups containing one to four carbon atoms, perfluoroalkyl groups containing one to four carbon atoms, alkoxy groups containing one to four carbon atoms, monohydroxyalkoxy groups containing two to four carbon atoms, dihydroxyalkoxy groups containing three to four carbon atoms and halogens, and, in addition to a member selected from the group consisting of water, aliphatic alcohols and mixtures of water and said alcohols; one or more additives selected from the group consisting of glycerin, glycols, glycol ethers, hair care materials, wetting agents and emulsifiers; anionic, cationic, amphoteric and nonionogenic surface active substances, thickeners, softeners, preservatives, complexing agents and perfumes.

4. A hair dyeing composition according to claim 3, further comprising a synthetic or natural polymer selected from the group consisting of chitosan, chitosan derivatives, polyvinyl pyrrolidone, polyvinyl acetate, polyvinyl alcohol, polyacrylic acid, polymethacrylic acid polyacrylic nitrile, polyvinyl lactam and copolymers thereof.

5. A hair dyeing composition according to claim 3, further comprising an oxidizing hair dye selected from the group consisting of p-Toluenediamine, p-Pheneylenediamine, p-Aminophenol, m-Pheneylenediamine, Resorcinol and m-Aminophenol.

6. A method of dyeing hair comprising the step of:
a. applying to said hair a hair dyeing composition containing 0.01 to 2.0% by weight of a 2,6-Dinitrophenol derivative of the general formula (I):

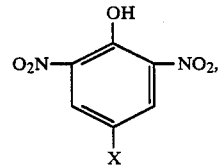

wherein X represents a member selected from the group consisting of an alkyl group containing one to four carbon atoms, a monohydroxyalkyl group containing one to four carbon atoms, a perfluoroalkyl group containing one to four carbon atoms, alkoxy group containing one to four carbon atoms, a monohydroxyalkoxy group containing two to four carbon atoms, dihydroxyalkoxy group containing three to four carbon atoms and halogen.

7. A hair dyeing composition according to claim 3, further comprising a hair dye selected from the group consisting of 2-Amino-4-nitro-phenol, picramic acid, 2-(2'-Hydroxyethyl)-amino-4,6-dinitro-benzene, 1-(2'-Hydroxyethyl)amino-2-amino-4-nitro-benzene, 4-(2'-Ureidoethyl)amino-nitro-benzene, 4(2', 3'-Dihydroxypropyl)amino-3- nitro-trifluoromethyl benzene, 1,4-Bis(2'-Hydroxyethyl)amino-4-N-ethyl-2-nitro-enzene, 4-(2'-Hydroxyethyl)amino-3-nitro-toluene, 2-Nitro-4-(b 2'-hydroxyethyl)amino-aniline, 2,5-Bis(2'-Hydroxyethyl)amino-nitro-benzene, 2-(2'-Hydroxyethyl)amino-4,6-dinitro-phenol, 1-Amino-4-(2', 3'-dihydroxypropyl)amino-2-nitro-5-chloro-benzene, 4-Bis(2'-hydroxyethyl)amino-1-(2'-hydroxyethyl)amino-2-nitro-benzene, 1-Amino-2-nitro-4-bis(2'-hydroxyethyl)amino-benzene, Basic Violet 1 (C.I. 42535), Acid Brown 4 (C.I. 14805), Disperse Blue 23 (C.I. 61545), Disperse Violet 4 (C.I. 61105), 1,4,5,8-tetraaminoanthraquinone and 1,4- diaminoanthraquinone.

8. A hair dyeing composition containing from 0.01 to 2.0% by weight of a 2,6-Dinitro-phenol derivative of the general formula (I):

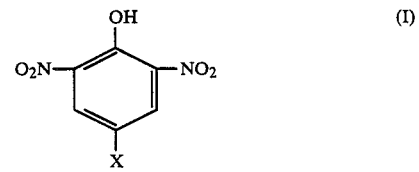

wherein X represents a member selected from the group consisting of alkyl groups containing one to four carbon atoms, monohydroxyalkyl groups containing one to four carbon atoms, perfluoroalkyl groups containing one to four carbon atoms, alkoxy groups containing one to four carbon atoms, monohydroxyalkoxy groups containing two to four carbon atoms, dihydroxyalkoxy groups containing three to four carbon atoms and halogens; and a hair dye selected from the group consisting of of 2-Amino-4-nitro-phenol, picramic acid, 2-(2'-Hydroxyethyl)-amino-4,6-dinitro-benzene, 1-(2'-Hydroxyethyl)amino-2-amino-4-nitro-benzene, 4-(2'-Ureidoethyl)amino-nitro-benzene, 4(2', 3'-Dihydroxypropyl)amino-3- nitro-trifluoromethyl benzene, 1,4-Bis(2'-Hydroxyethyl)amino-4-N-ethyl-2-nitro-enzene, 4-(2'-Hydroxyethyl)amino-3-nitro-toluene, 2-Nitro-4-(b 2'-hydroxyethyl)amino-aniline, 2,5-Bis(2'-Hydroxyethyl)amino-nitro-benzene, 2-(2'-Hydroxyethyl)amino-4,6-dinitro-phenol, 1-Amino-4-(2', 3'-dihydroxypropyl)amino-2-nitro-5-chloro-benzene, 4-Bis(2'-hydroxyethyl)amino-1-(2'-hydroxyethyl)amino-2-nitro-benzene, 1-Amino-2-nitro-4-bis(2'-hydroxyethyl)amino-benzene, Basic Violet 1 (C.I. 42535), Acid Brown 4 (C.I. 14805), Disperse Blue 23 (C.I. 61545), Disperse Violet 4 (C.I. 61105), 1,4,5,8-tetraaminoanthraquinone and 1,4- diaminoanthraquinone.

9. A hair dyeing composition containing from 0.01 to 2.0% of a 2,6-Dinitro-phenol derivative of the general formula (I):

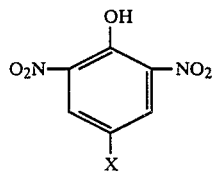

wherein X represents a member selected from the group consisting of alkyl groups containing one to four carbon atoms, monohydroxyalkyl groups containing one to four carbon atoms, perfluoroalkyl groups containing one to four carbon atoms, alkoxy groups containing one to four carbon atoms, monohydroxyalkoxy groups containing two to four carbon atoms, dihydroxyalkoxy groups containing three to four carbon atoms and halogens, and an oxidizing hair dye selected from the group consisting of P-Toluenediamine, p-Phenylenediamine, p-Aminophenol, m-Pheneylenediamine, Resorcinol and m-Aminophenol.

10. A hair dyeing composition according to claim 12, further comprising a natural or synthetic polymer selected from the group consisting of chitosan, chitosan derivatives, polyvinyl pyrrolidone, polyvinyl acetate, polyvinyl alcohol, polyacrylic acid, polymethacrylic acid, polyacrylic nitrile, polyvinyl lactam and copolymers thereof.

* * * * *